US010194882B2

(12) United States Patent
Kwak et al.

(10) Patent No.: US 10,194,882 B2
(45) Date of Patent: Feb. 5, 2019

(54) X-RAY IMAGING APPARATUS AND METHOD OF CONTROLLING THE SAME

(71) Applicant: SAMSUNG ELECTRONICS CO., LTD., Suwon-si (KR)

(72) Inventors: Ho-seong Kwak, Seoul (KR); Jin Ho Park, Suwon-si (KR); Seung Hoon Kim, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 133 days.

(21) Appl. No.: 14/878,187

(22) Filed: Oct. 8, 2015

(65) Prior Publication Data

US 2016/0220215 A1 Aug. 4, 2016

(30) Foreign Application Priority Data

Feb. 4, 2015 (KR) ........................ 10-2015-0017502

(51) Int. Cl.
*A61B 6/00* (2006.01)
*A61B 6/10* (2006.01)

(52) U.S. Cl.
CPC ................. *A61B 6/54* (2013.01); *A61B 6/10* (2013.01); *A61B 6/467* (2013.01); *A61B 6/589* (2013.01)

(58) Field of Classification Search
CPC ...................................................... A61B 6/102
See application file for complete search history.

(56) References Cited

U.S. PATENT DOCUMENTS

2004/0234039 A1 11/2004 Karaus et al.
2008/0013692 A1 1/2008 Maschke
2008/0242969 A1* 10/2008 Sayeh .................... A61B 6/032 600/407
2008/0304626 A1 12/2008 Camus
2011/0154569 A1 6/2011 Wiggers et al.
2013/0121477 A1* 5/2013 Lee .......................... H05G 1/02 378/198
2014/0072101 A1 3/2014 Park et al.
2014/0247918 A1 9/2014 Kang et al.
2015/0033195 A1 1/2015 Jin et al.

FOREIGN PATENT DOCUMENTS

KR 10-2009-0104393 A 10/2009

OTHER PUBLICATIONS

Communication dated Feb. 3, 2016 issued by the International Searching Authority in counterpart International Application No. PCT/KR2015/010836 (PCT/ISA/210).

* cited by examiner

*Primary Examiner* — Dani Fox
(74) *Attorney, Agent, or Firm* — Sughrue Mion, PLLC

(57) ABSTRACT

Disclosed herein are an X-ray imaging apparatus and a method for controlling the X-ray imaging apparatus. A path on which an X-ray source avoids an obstacle is automatically set on a movement path of the X-ray source, or a user sets the path manually by using simple manipulation so that an efficient X-ray imaging system can be provided. The X-ray imaging apparatus includes: an X-ray source movably disposed; a manipulation unit through which control instructions relating to a movement region of the X-ray source are input; and a processor that controls at least one movement of the X-ray source so that the X-ray source is moved within the movement region based on the inputted control instructions.

24 Claims, 13 Drawing Sheets

(a)

(b)

(a) SET MOVEMENT LIMITATION DIRECTION (b) SET AVOIDANCE PATH (a) EXISTING (b) AFTER RESETTING

X-RAY IMAGING APPARATUS AND METHOD OF CONTROLLING THE SAME

CROSS-REFERENCE TO RELATED APPLICATION

This application claims priority from Korean Patent Application No. 10 2015-0017502, filed on Feb. 4, 2015 in the Korean Intellectual Property Office, the disclosure of which is incorporated herein by reference in its entirety.

BACKGROUND

1. Field

Exemplary embodiments relate to an X-ray imaging apparatus that generates an X-ray image by radiating X-rays onto an object and a method of controlling the same.

2. Description of the Related Art

X-ray imaging apparatuses are apparatuses that obtain an image of an inside of an object by using X-rays. Such X-ray imaging apparatuses capture an image inside the object using non-invasive methods, whereby X-rays are radiated onto the object and the X-rays transmitted by the object are detected. Thus, these X-ray imaging apparatuses for medical purposes can be used to diagnose an injury or a disease inside the object that cannot be checked from the exterior.

Each of the X-ray imaging apparatuses includes an X-ray source that generates X-rays and radiates the X-rays onto the object, and an X-ray detector that detects X-rays that propagate through the object. The X-ray source may be movably disposed so as to image various parts of the object. The X-ray detector can be used in a table mode in which the X-ray detector is mounted on an image capturing table, in a stand mode in which the X-ray detector is mounted on an image capturing stand, or in a portable mode in which the X-ray detector is not fixed in any one position. Two or more X-ray detectors may be disposed for one X-ray source.

These X-ray imaging apparatuses are recently digitalized, and an X-ray image obtained using a film method according to the related art has been obtained using a digital method, and simultaneously, many parts of the X-ray imaging apparatus have been automatized. Examples of this automation include an auto tracking function in which the X-ray source automatically tracks the X-ray detector, and an auto centering function in which positions of the X-ray source and the X-ray detector are automatically adjusted. In order to implement an automation function of the X-ray imaging apparatus, such as auto tracking or auto centering, to freely move the X-ray source and to prevent re-imaging, the position of an obstacle placed on a movement path should be checked and moved without collision with the X-ray source while the X-ray source is moved.

SUMMARY

Therefore, it is an aspect of one or more exemplary embodiments to provide an X-ray imaging apparatus, whereby, while an X-ray source is moved for X-ray imaging, the position of an obstacle placed on a movement path is checked, a path on which the X-ray source avoids the obstacle is stored, and movement of the X-ray source is controlled according to the stored path, and a method of controlling the X-ray imaging apparatus.

Additional aspects of the exemplary embodiments will be set forth in part in the description which follows and, in part, will be apparent from the description, or may be learned by practice of the exemplary embodiments.

In accordance with one aspect of one or more exemplary embodiments, an X-ray imaging apparatus includes: an X-ray source which is movably disposed; an input device configured to receive at least one control instruction relating to a movement region of the X-ray source; and a processor configured to control a movement of the X-ray source such that the X-ray source is moved within the movement region based on the at least one control instruction.

The input device may include a touch screen that is disposed within a predetermined proximity of the X-ray source and that is configured to provide an interface via which the at least one control instruction is inputtable.

The input device may be further configured to receive at least one instruction that relates to resetting the movement region of the X-ray source as a region that excludes an object that exists in a movement path of the X-ray source.

The input device may include: a first button via which at least one instruction relating to a control mode of the movement region is inputtable; and a second button via which at least one instruction relating to storing data that relates to the movement region of the X-ray source based on the at least one control instruction is inputtable.

If the first button is manipulated, at least one control instruction that relates to setting a direction in which a movement of the X-ray source is limited, or to setting a movement path of the X-ray source may be received, and each of the first button and the second button may include at least one from among a physical input unit, a touch screen and a remote controller.

The processor may be further configured to reset a shortest path on which the X-ray source is moved to a target point within the movement region based on the received at least one control instruction, and to control a movement of the X-ray source so that the X-ray source is moved based on the reset path.

The X-ray imaging apparatus may further include a memory configured to store data that relates to the movement region of the X-ray source based on the received at least one control instruction.

The memory may be further configured to store data that relates to the reset path.

In accordance with another aspect of one or more exemplary embodiments, an X-ray imaging apparatus includes: an X-ray source which is movably disposed; a sensor configured to detect an object which is disposed within a first predetermined proximity of the X-ray source; and a processor configured to control a movement of the X-ray source such that when the object is detected by the sensor, the X-ray source is moved so as to avoid the object.

The sensor may be disposed within a second predetermined proximity of the X-ray source and may include at least one from among a motion sensor, an image sensor, an infrared sensor, a radio sensor and a three-dimensional (3D) detection sensor.

The sensor may be further configured to detect a distance between the X-ray source and the object and to detect the object while the X-ray source is being moved so as to avoid the object.

The processor may be further configured to reset a shortest path on which the X-ray source is moved to a target point while avoiding the object, and to control a movement region of the X-ray source such that the X-ray source is moved based on the reset path.

The X-ray imaging apparatus may further include a memory configured to store data that relates to the movement region of the X-ray source.

The memory may be further configured to store data that relates to the reset path.

In accordance with still another aspect of one or more exemplary embodiments, a method for controlling an X-ray imaging apparatus, includes: moving an X-ray source to be adjacent to an object; receiving at least one control instruction relating to a movement region of the X-ray source; and controlling a movement of the X-ray source such that the X-ray source is moved within the movement region based on the received at least one control instruction.

The receiving the at least one control instruction may include receiving at least one control instruction that relates to at least one from among setting a direction in which a movement of the X-ray source is limited and setting a movement path of the X-ray source.

The controlling the movement of the X-ray source may include resetting a shortest path on which the X-ray source is moved to a target point within the movement region based on the received at least one control instruction and controlling the movement of the X-ray source such that the X-ray source is moved based on the reset path.

The method may further include storing data that relates to the movement region of the X-ray source based on the received at least one control instruction.

The storing the data may further include storing data that relates to the reset path.

In accordance with yet still another aspect of one or more exemplary embodiments, a method for controlling an X-ray imaging apparatus includes: moving an X-ray source to be adjacent to an object; detecting an object that is disposed within a predetermined proximity of the X-ray source; and controlling a movement of the X-ray source such that the X-ray source is moved so as to avoid the detected object.

The detecting the object may include detecting a distance between the X-ray source and the object and detecting the object while the X-ray source is being moved so as to avoid the object.

The controlling the movement of the X-ray source may include resetting a shortest path on which the X-ray source is moved to a target point so as to avoid the detected object and controlling the movement of the X-ray source such that the X-ray source is moved based on the reset path.

The method may further include storing data that relates to a movement region of the X-ray source.

The storing the data may include storing data that relates to the reset path.

BRIEF DESCRIPTION OF THE DRAWINGS

These and/or other aspects will become apparent and more readily appreciated from the following description of exemplary embodiments, taken in conjunction with the accompanying drawings of which.

DETAILED DESCRIPTION

Figure 1:
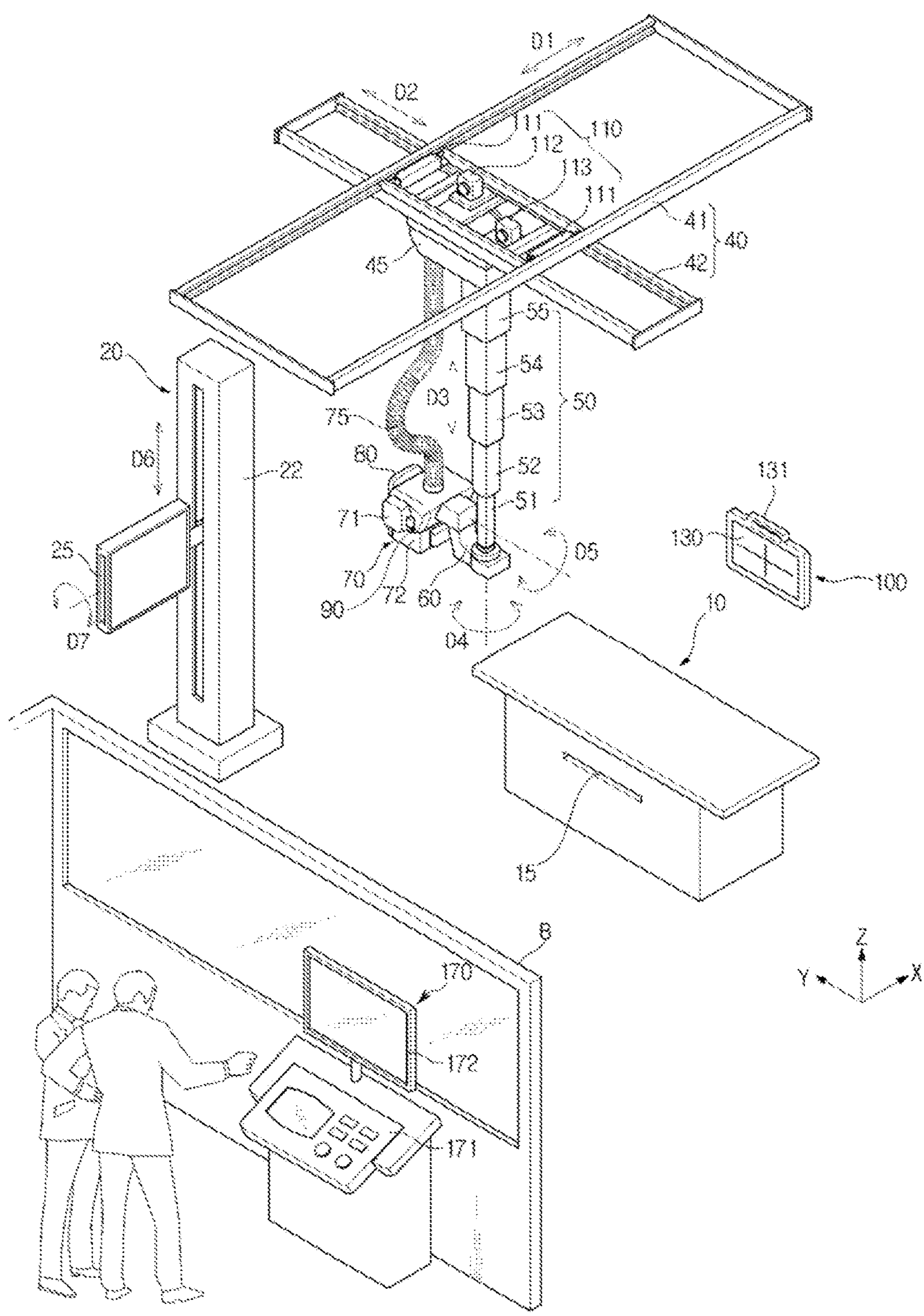
FIG. 1 is a perspective view of an X-ray imaging apparatus, in accordance with an exemplary embodiment.

According to an obstacle collision prevention method of an X-ray imaging apparatus according to the related art, when an object is placed on a movement path of the X-ray imaging apparatus, if sensor signals for detecting the object are obtained using a sensor mounted in the X-ray imaging apparatus in a predetermined range, a movement of the X-ray imaging apparatus is stopped, and a collision with an obstacle is prevented. In this case, in order to move the X-ray imaging apparatus so as to avoid the obstacle, a system engineer resets a path on which the X-ray imaging apparatus avoids the obstacle, by performing a separate task on the X-ray imaging apparatus.

According to such an obstacle collision prevention system, when the object is detected by the sensor while the X-ray imaging apparatus is being moved, the X-ray imaging apparatus does not avoid the object, is not moved, and is stopped, such that a time delay occurs in X-ray imaging and diagnosis. Further, when the path on which the X-ray imaging apparatus avoids the obstacle is not reset, a movement of the X-ray imaging apparatus can be performed on a predetermined path and in a predetermined region, which is inefficient. When the system engineer works to reset the path on which the X-ray imaging apparatus avoids the obstacle, a predetermined amount of time is required, and continuous use of the X-ray imaging apparatus and X-ray imaging diagnosis cannot be performed.

In this aspect, there is no problem in avoiding the object on the movement path and a movement region of the X-ray imaging apparatus and moving the X-ray imaging apparatus. However, there is a limitation in resetting the movement path in real time so that the X-ray imaging apparatus is moved so as to avoid a new obstacle while an X-ray imaging and diagnosis operation is being performed.

Thus, an efficient method for resetting a path on which the X-ray imaging apparatus is moved so as to avoid a new obstacle, when the new obstacle exists in the movement path of the X-ray imaging apparatus even during a performance of an X-ray imaging procedure or an X-ray diagnosis procedure, is necessary.

Reference will now be made in detail to exemplary embodiments, examples of which are illustrated in the accompanying drawings, wherein like reference numerals refer to like elements throughout, and a redundant description thereof will be omitted.

Hereinafter, an X-ray imaging apparatus and a method for controlling the same according to the following exemplary embodiments will be described in detail with reference to the attached drawings.

Figure 2:
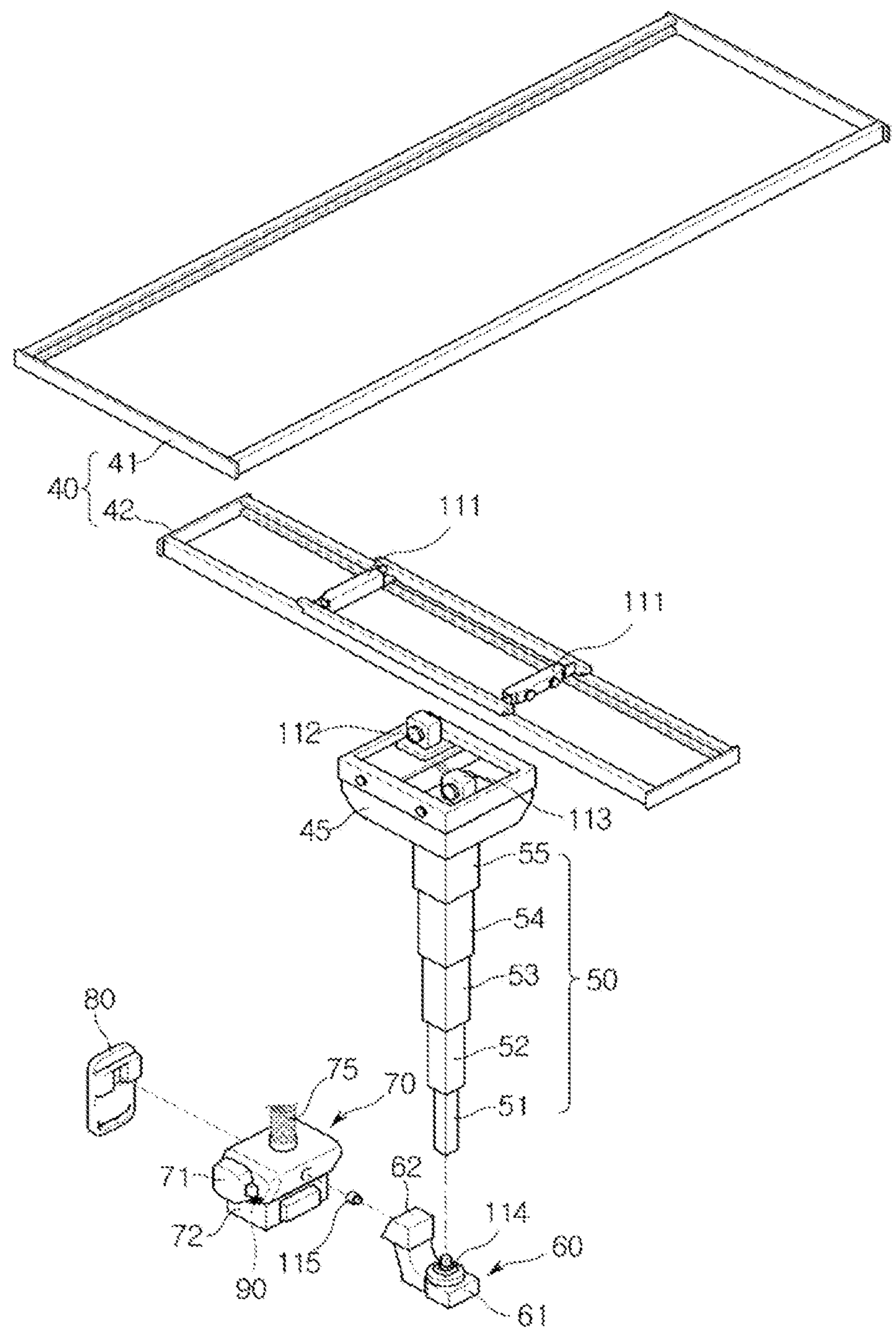
FIG. 2 is an exploded perspective view of the X-ray imaging apparatus illustrated in FIG. 1.
Figure 3:
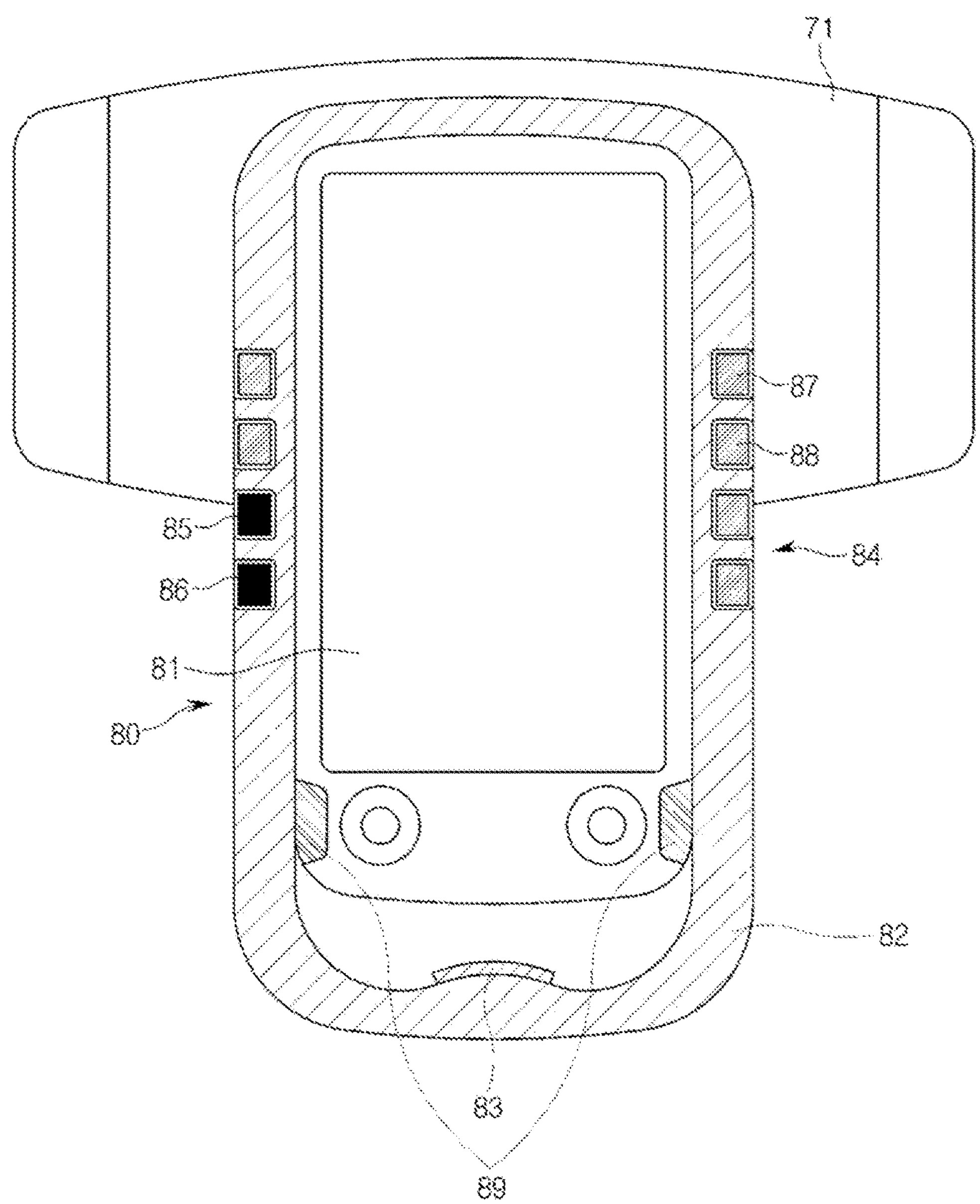
FIG. 3 is a front view of a manipulation unit of the X-ray imaging apparatus of FIG. 1.

FIG. 1 is a perspective view of an X-ray imaging apparatus, in accordance with an exemplary embodiment, and FIG. 2 is an exploded perspective view of the X-ray imaging apparatus illustrated in FIG. 1, and FIG. 3 is a front view of a manipulation unit of the X-ray imaging apparatus of FIG. 1.

Referring to FIGS. 1, 2, and 3, an X-ray imaging apparatus 1 may include a guide rail 40, a movement carriage 45, a postframe 50, motors 111, 112, 113, 114, and 115, an X-ray source 70, an X-ray detector 100, a manipulation unit (also referred to herein as an "input device") 80, and a workstation 170. The X-ray imaging apparatus 1 may further include an image capturing table 10 and an image capturing stand 20 on which the X-ray detector 100 may be mounted.

The guide rail 40, the movement carriage 45, and the postframe 50 are disposed to move the X-ray source 70 toward an object.

The guide rail 40 includes a first guide rail 41 and a second guide rail 42 installed to form a predetermined angle with respect to each other. The first guide rail 41 and the second guide rail 42 may extend in a direction in which they meet at right angles.

The first guide rail 41 is installed on a ceiling of an inspection room in which a radiographic imaging apparatus is disposed.

The second guide rail 42 is placed at a lower side of the first guide rail 41 and is slidably mounted on the first guide rail 41. A roller (not shown) that is movable along the first guide rail 41 may be installed on the first guide rail 41. The second guide rail 42 may be connected to the roller (not shown) and may move along the first guide rail 41.

A first direction D1 is defined as a direction in which the first guide rail 41 extends, and a second direction D2 is defined as a direction in which the second guide rail 42 extends. Thus, the first direction D1 and the second direction D2 may meet at right angles and may be parallel to the ceiling of the inspection room.

The movement carriage 45 is disposed at a lower side of the second guide rail 42 so as to be movable along the second guide rail 42. A roller (not shown) may be installed in the movement carriage 45 so as to move along the second guide rail 42. Thus, the movement carriage 45 is movable together with the second guide rail 42 in the first direction D1 and is movable along the second guide rail 42 in the second direction D2. The postframe 50 is fixed to the movement carriage 45 and is placed at a lower side of the movement carriage 45. The postframe 50 may include a plurality of posts 51, 52, 53, 54, and 55.

The plurality of posts 51, 52, 53, 54, and 55 may be foldably or nestably connected to one another, and the length of the postframe 50 may be increased or decreased in a vertical direction of the inspection room while the postframe 50 is fixed to the movement carriage 45.

A third direction D3 is defined as a direction in which the length of the postframe 50 is increased or decreased. Thus, the third direction D3 may meet the first direction D1 and the second direction D2 at right angles.

The X-ray source 70 is an apparatus that radiates X-rays onto an object. In this aspect, the object may be a living body of the human being or animal, but is not limited thereto. Any thing, an internal structure of which can be imaged by the X-ray imaging apparatus 1, may be used as the object.

The X-ray source 70 may include an X-ray tube 71 that generates X-rays and a collimator 72 that guides the generated X-rays toward the object. A collision sensor 90 that may detect a collision may be disposed in the X-ray tube 71, as illustrated in FIGS. 1 and 2. The position of the collision sensor 90 illustrated in FIGS. 1 and 2 is just illustrative, and the collision sensor 90 may be disposed in a different position.

A rotation joint 60 is disposed between the X-ray source 70 and the postframe 50.

The rotation joint 60 enables the X-ray source 70 to be combined with the postframe 50 and supports a load applied to the X-ray source 70.

The rotation joint 60 may include a first rotation joint 61 connected to a bottom post 51 of the postframe 50 and a second rotation joint 62 connected to the X-ray source 70.

The first rotation joint 61 is disposed to be rotatable about a central axis of the postframe 50 that extends in the vertical direction of the inspection room. Thus, the first rotation joint 61 may be rotated on a plane that is perpendicular to the third direction D3. In this case, a rotation direction of the first rotation joint 61 may be newly defined. A fourth direction D4 that is newly defined is a rotation direction of an axis that is parallel to the third direction D3.

The second rotation joint 62 is disposed to be rotatable on a plane that is perpendicular to the ceiling of the inspection room. Thus, the second rotation joint 62 may rotate in a rotation direction of an axis that is parallel to the first direction D1 or the second direction D2. In this case, a rotation direction of the second rotation joint 62 may be newly defined. A fifth direction D5 that is newly defined is a rotation direction of an axis that extends in the first direction D1 or the second direction D2. The X-ray source 70 may be connected to the rotation joint 60 and may be moved by rotation in the fourth direction D4 and the fifth direction D5. Further, the X-ray source 70 may be connected to the postframe 50 by using the rotation joint 60, and may make a straight motion in the first direction D1, the second direction D2, and the third direction D3.

A motor 110 may be disposed to move the X-ray source 70 in any of the first through fifth directions D1, D2, D3, D4, and D5. The motor 110 may be a motor that is electrically driven, and an encoder may be included in the motor 110.

The motor 110 may include first, second, third, fourth, and fifth motors 111, 112, 113, 114, and 115 to correspond to the first through fifth directions D1, D2, D3, D4, and D5, respectively.

Each of the motors 111, 112, 113, 114, and 115 may be disposed in any of various positions in consideration of convenience of design. For example, the first motor 111 that moves the second guide rail 42 in the first direction D1 may be disposed around (i.e., in close proximity to) the first guide rail 41, and the second motor 112 that moves the movement carriage 45 in the second direction D2 may be disposed around the second guide rail 42, and the third motor 113 that increases or decreases the length of the postframe 50 in the third direction D3 may be disposed in the movement carriage 45. The fourth motor 114 that moves the X-ray source 70 by rotation in the fourth direction D4 may be disposed around the first rotation joint 61, and the fifth motor 115 that moves the X-ray source 70 by rotation in the fifth direction D5 may be disposed around the second rotation joint 62.

Each motor 110 may be connected to a power transmission unit (also referred to herein as a "power transmitter") (not shown) so as to make a straight or rotation motion of the X-ray source 70 in the first through fifth directions D1 through D5. The power transmission unit (not shown) may include a belt and a pulley, a chain and a sprocket, and a shaft, which are generally used.

The manipulation unit 80 that provides a user interface may be disposed at one side of the X-ray source 70. In this aspect, a user who performs diagnosis of the object by using the X-ray imaging apparatus 1 may be a member of a medical team that includes a doctor, a radiologist, and a nurse. However, the exemplary embodiments are not limited thereto, and anyone who uses the X-ray imaging apparatus 1 may be the user.

The manipulation unit 80 may include a display unit (also referred to herein as a "display device" and/or as a "display") 81 that provides an interface via which various information that relates to X-ray imaging may be input or each device may be manipulated and controlled, buttons 84 for manipulating devices or inputting control instructions, and sensors 89 that may detect a collision with the object, as illustrated in FIG. 3, so that the user may input various information that relates to X-ray imaging or may manipulate each device. Further, the user may input control instructions in a movement region of the X-ray source 70 by using the manipulation unit 80. In this case, the display unit 81 may be implemented with a touch panel via which the user may touch a screen and input control instructions. The display unit 81 may include any of a cathode ray tube (CRT), a liquid crystal display (LCD), or an organic light emitting diode (LED). However, the exemplary embodiments are not limited thereto. In addition, the display unit 81 may include a touch screen via which the user's touch gesture may be input. Soft key type buttons that perform the same functions as those of all physical buttons 84 for manipulating each device may be implemented on the touch screen. The user touches the buttons implemented on the touch screen, thereby inputting the same instructions as those for manipulating the physical buttons.

The buttons 84 may include rotation selection buttons 85 and 86 which are manipulated when the user wants to rotate the X-ray source 70 in the fourth direction D4 or the fifth direction D5. In particular, when the user wants to rotate the X-ray source 70 in the fourth direction D4, the user may rotate the X-ray source 70 in the fourth direction D4 after pressing a fourth direction rotation selection button 85, or may rotate the X-ray source 70 in the fourth direction D4 while pressing the fourth direction rotation selection button 85, and when the user wants to rotate the X-ray source 70 in the fifth direction D5, the user may rotate the X-ray source 70 in the fifth direction D5 after pressing a fifth direction rotation selection button 86, or may rotate the X-ray source 70 in the fifth direction D5 while pressing the fifth direction rotation selection button 86. Positions of the rotation selection buttons 85 and 86 illustrated in FIG. 3 are just examples, and the rotation selection buttons 85 and 86 may be disposed in different positions, and soft key type buttons that perform the same functions as those of the rotation selection buttons may be implemented on the touch screen.

The buttons 84 may include a first button 87 via which the user receives instructions that relate to a control mode of the movement region of the X-ray source 70, and a second button 88 via which the user receives instructions for storing data that relates to the movement region of the X-ray source 70 based on the input control instructions. The user may set a direction or a movement path of the X-ray source 70 by pressing the first button 87 in order to move the X-ray source 70 so as to avoid the object (obstacle) placed on the movement path of the X-ray source 70. In particular, the user may press the first button 87 and then may press another button 84 according to the screen relating to the control instructions displayed on the display unit 81, or may directly touch the screen, thereby inputting control instructions that relate to the movement region of the X-ray source 70. Further, the user may press the second button 88, thereby storing data that relates to the movement region of the X-ray source 70 based on the input control instructions. Positions of the first button 87 and the second button 88 illustrated in FIG. 3 are just examples, and of course, the first button 87 and the second button 88 may be disposed in different positions. As illustrated in FIG. 3, the user may also be provided with the interface which is displayed in the form of a touch screen on the display unit 81 and via which the control instructions relating to the movement region of the X-ray source 70 are inputtable, in addition to the buttons 84 as physical input units.

The sensors 89 placed in the manipulation unit 80 perform a function of preventing a collision between the X-ray source 70 and the object placed on the movement path of the X-ray source 70. Positions of the sensors 89 are not limited, and the sensors 89 may be installed in any position of the manipulation unit 80. Further, the number of installed sensors 89 is not limited. A description of the function of the sensors 89 will be described below.

The manipulation unit 80 may include a handle 82 that the user may grasp. The user may grasp the handle 82 of the manipulation unit 80 and may apply a force or torque to the X-ray source 70 so as to move the X-ray source 70. This is defined as a manual movement mode, and an automatic movement mode will be defined by a motor controller (not shown) included in a processor 300 that will be described below. In FIG. 3, the handle 82 is disposed at a lower portion of the manipulation unit 80. However, this is just an example, and the handle 82 may also be disposed in a different position of the manipulation unit 80.

Further, the manipulation unit 80 may include a mode conversion unit (also referred to herein as a "mode converter") 83 which is configured for converting between a manual movement mode in which the X-ray source 70 is manually moved, and an automatic movement mode in which the X-ray source 70 is automatically moved. The mode conversion unit 83 having a switch shape may be disposed in the handle 82 of the manipulation unit 80, and a detailed description of movement of the X-ray source 70 with respect to each of the manual movement mode and the automatic movement mode will be described below.

The X-ray detector 100 is a device that detects X-rays that have propagated through the object. An incidence surface 130, on which the X-rays are incident, is defined on a front surface of the X-ray detector 100, and a detection panel (not shown) is disposed in the X-ray detector 100. A plurality of pixels that respond to the X-rays may be arranged on the detection panel to have a matrix shape. A handle 131 may be disposed in the center of a top end of the X-ray detector 100 so that the user may move or carry the X-ray detector 100.

The X-ray detector 100 may operate in any of various imaging modes according to its position when X-ray imaging is performed. In detail, the X-ray detector 100 may operate in a table mode in which the X-ray detector 100 is mounted on the image capturing table 10, or in a stand mode in which the X-ray detector 100 is mounted on the image capturing stand 20, or may not be mounted on the image capturing table 10 or image capturing stand 20 but may operate in a portable mode in which the X-ray detector 100 is disposed in an arbitrary position according to the position of the object and a part to be imaged of the object. In particular, accommodation portions 15 and 25 may be disposed in the image capturing table 10 and the image capturing stand 20, respectively, so that the X-ray detector 100 may be mounted on the image capturing table 10 or image capturing stand 20. An accommodation portion disposed in the image capturing table 10 may be defined as a first accommodation portion 15, and an accommodation portion disposed in the image capturing stand 20 may be defined as a second accommodation portion 25. The second accommodation portion 25 is disposed to be movable in a lengthwise direction of a support 22 and to be rotatable in a rotation direction of an axis that is perpendicular to the lengthwise direction of the support 22, as illustrated in FIG. 1. In this case, the lengthwise direction of the support 22 may be defined as a sixth direction D6, and the rotation direction of an axis that is perpendicular to the sixth direction D6 may be defined as a seventh direction D7.

The workstation 170 includes an input unit 171 and a display unit 172 and provides a user interface, similarly as in the manipulation unit 80. Thus, the user may input various information that relates to X-ray imaging by using the workstation 170, or may manipulate devices. Furthermore, the user may input various instructions relating to an operation of the X-ray imaging apparatus 1 by using the workstation 170, for example, instructions that relate to selecting an image capturing position or instructions that relate to starting an X-ray imaging process. Further, the user may check an image acquired when X-ray imaging is performed by using the workstation 170.

The input unit 171 may include at least one of a switch, a keyboard, a track ball, a mouse, and a touch screen. When the input unit 171 is implemented with a graphical user interface (GUI), such as a touch screen, i.e., software, the input unit 171 may be displayed on the display unit 172. The display unit 172 may include any of a CRT, an LCD or an organic LED, like in the display unit 81. However, the exemplary embodiments are not limited thereto.

Further, various types of processing units, such as a central processing unit (CPU) or a graphic processing unit (GPU), and a printed circuit board (PCB) may be built in the workstation 170, and various kinds of storing units may also be built in the workstation 170 as needed. Thus, a main component of the X-ray imaging apparatus 1, for example, a processor (300 of FIG. 4) may be disposed in the workstation 170 so that various determinations for the operation of the x-ray imaging apparatus 1 may be performed, or various control signals may be generated.

The workstation 170 having the above configuration may be disposed in a separate independent space B in which the X-rays are blocked. The workstation 170 may be connected to the X-ray source 70 and the X-ray detector 100 via wired communication and/or wireless communication.

Figure 4:
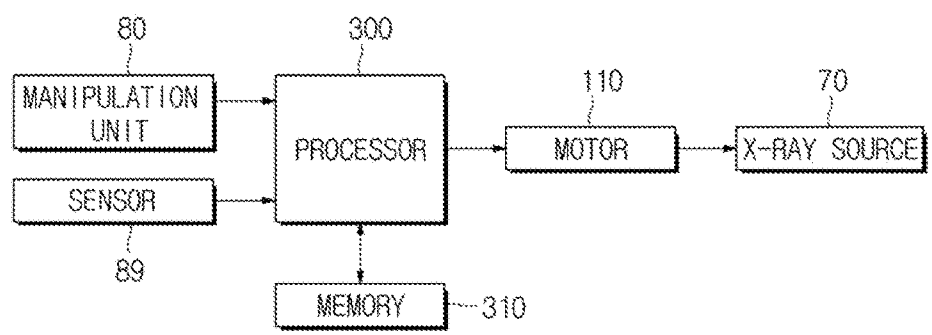
FIG. 4 is a control block diagram of a configuration of an X-ray imaging apparatus, in accordance with an exemplary embodiment.

FIG. 4 is a control block diagram of a configuration of an X-ray imaging apparatus, in accordance with an exemplary embodiment.

As illustrated in FIG. 4, the X-ray imaging apparatus 1 according to an exemplary embodiment may include a manipulation unit (also referred to herein as an "input device") 80 that provides an interface via which various information that relates to X-ray imaging may be input or devices may be manipulated and controlled and control instructions that relate to the movement region of the X-ray source 70 may be input, and sensors 89 that prevent a collision between the X-ray source 70 and an object and detect an obstacle placed on a periphery or movement path of the X-ray source 70. In addition, the X-ray imaging apparatus 1 may further include a processor 300 that generates control signals to enable the X-ray source 70 to avoid the obstacle and to be moved based on the movement control instructions of the X-ray source 70 input via the manipulation unit 80 or a detection of an object by the sensors 89, and that resets a shortest path on which the X-ray source 70 avoids the obstacle and is moved to a target point, a motor 110 that provides a driving force for moving the X-ray source 70 based on the control signals of the processor 300, a memory 310 in which data that relates to the movement region of the X-ray source 70 that avoids the obstacle and is moved and data that relates to the shortest path reset so that the X-ray source 70 may be moved to the target point are stored, and an X-ray source 70 that is disposed to be movable, radiates X-rays onto the object and images the object.

Hereinafter, each configuration of the X-ray imaging apparatus 1 according to an exemplary embodiment and a method for controlling the X-ray imaging apparatus 1 will be described in detail with reference to FIGS. 5 through 13.

Figure 5:
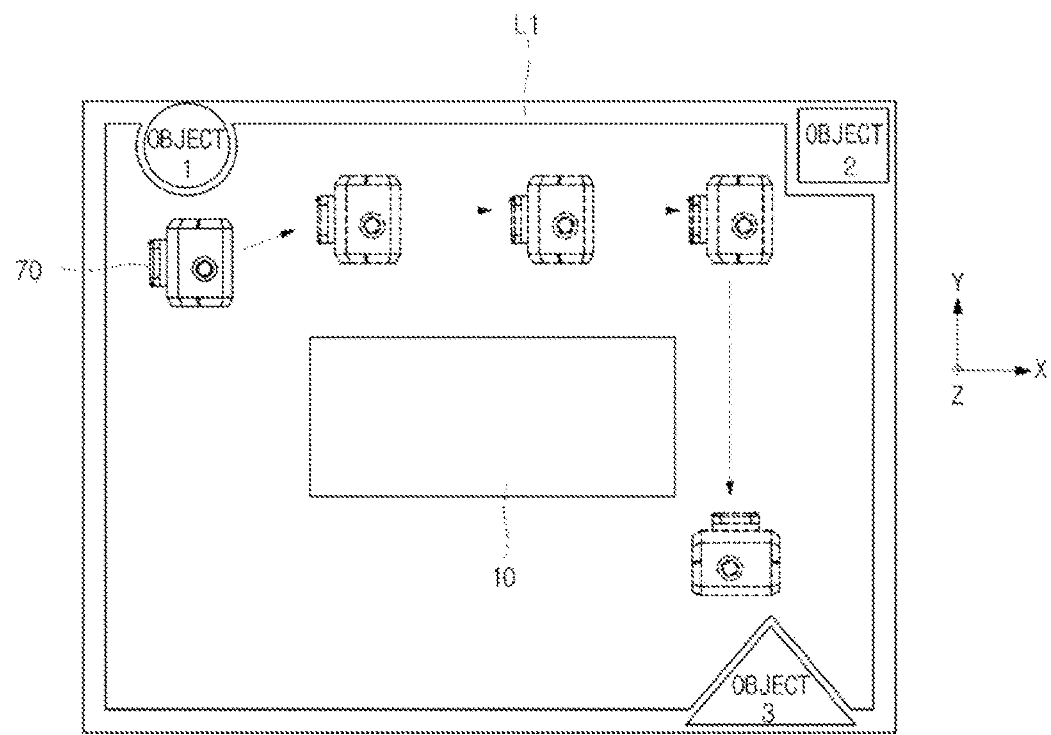
FIG. 5 is a view showing a case in which an X-ray source is moved to a predetermined path, in accordance with an exemplary embodiment.

FIG. 5 is a view showing a case in which an X-ray source is moved to a predetermined path, in accordance with an exemplary embodiment.

FIG. 5 is a top view illustrating a case in which the X-ray source 70 is moved within a region that includes the image capturing table 10 upon which an object to be imaged may be placed. As illustrated in FIG. 5, the X-ray imaging apparatus 1 and the image capturing table 10 may be disposed in an X-ray image capturing room for X-ray imaging, and objects 1, 2, and 3 may be disposed at the X-ray imaging apparatus 1 and the image capturing table 10. The X-ray source 70 may be moved to perform X-ray imaging for the object, and a movement direction is based on movement in directions of an X-axis, a Y-axis, and a Z-axis. However, when movement in three directions is simultaneously performed, the X-ray source 70 may be moved on a path that has a curved shape. Thus, the movement direction and a movement shape are not limited.

The X-ray imaging apparatus 1 may include the processor 300 that is electrically connected to devices disposed in the X-ray imaging apparatus 1, such as the motor 110 and the manipulation unit 80 and that controls the devices. The processor 300 may be disposed in the movement carriage 45. However, the position of the processor 300 is not limited thereto, but may also be disposed in the manipulation unit 80. The processor 300 may drive each motor 110 to move the X-ray imaging apparatus 1 to a desired position. For example, when the user inputs a desired image capturing position via the manipulation unit 80, the processor 300 operates the motor 110 required for movement of an image capturing unit based on information that relates to a current position and the input image capturing position. As the motor 110 operates, the X-ray source 70 may be automatically moved to the user's desired image capturing position. This is referred to as an automatic movement mode. Further, even when the X-ray source 70 is to be placed at a particular point in addition to inputting a desired image capturing position, the X-ray source 70 may be moved to the desired position by using manipulation of the manipulation unit 80. The user may select the automatic movement mode remotely using a remote controller (not shown) which has an interface via which instructions for moving the X-ray source 70 to a desired position may be input. Alternatively, the user may also input instructions for operating the automatic movement mode by using the manipulation unit 80 or the workstation 170.

In addition, the user may move the X-ray source 70 by directly applying a force or torque to the X-ray source 70. This is referred to as a manual movement mode. In the manual movement mode, the user may grasp the handle 82 disposed in the manipulation unit 80 and may physically move the X-ray source 70 to the desired position. In order to convert the automatic movement mode into the manual movement mode, the mode conversion unit 83 may be disposed. The mode conversion unit 83 having a switch shape may be disposed in the handle 82 of the manipulation unit 80. The user may press the mode conversion unit 83 by grasping the handle 82 so as to convert the automatic movement mode into the manual movement mode, or may release the handle 82 so as to convert the manual movement mode into the automatic movement mode. Further, even when the user does not grasp the handle 82, i.e., does not press the mode conversion unit 83 so as to apply the force or torque to the X-ray source 70, the processor 300 may convert the automatic movement mode into the manual movement mode by calculating the force or torque via application of an algorithm.

In the manual movement mode, the user may need a relatively large force or torque for moving the position of the X-ray source 70 so as to overcome a frictional force generated in a periphery of each motor 110. In this case, when the user applies the force or torque to the X-ray source 70 in the manual movement mode, the user may detect the user's force or torque and may provide a power assistant mode in which the motor 110 is operated according to the detected force or torque. In the power assistant mode, the user may move the X-ray source 70 by using a small force or torque applied by a driving force of the motor 110. In this case, a sensor, such as a fork/torque sensor, may be used to directly measure the force and torque.

As illustrated in FIG. 5, a path L1 on which the X-ray source 70 may be moved so as to avoid the objects 1, 2, and 3 may be previously set. Since the shapes of the objects placed on the path L1 on which the X-ray source 70 is moved may be diverse, a path set to avoid the objects 1, 2, and 3 may be set in various ways. The X-ray source 70 may be moved in an arbitrary direction, such as on a path indicated by dotted lines in a region that includes the set path L1. The X-ray source 70 may be moved by the above-described manual movement mode or automatic movement mode, and the sensor 89 disposed in the manipulation unit 80 may detect an object placed on the movement path while the X-ray source 70 is being moved. As described above with respect to FIGS. 1,2, and 3, the sensors 89 and 90 that detect the object to prevent a collision may be disposed in an arbitrary position of the X-ray source 70. However, for convenience of explanation, an exemplary embodiment in which the sensor 89 is disposed in the manipulation unit 80 will now be described.

Figure 6:
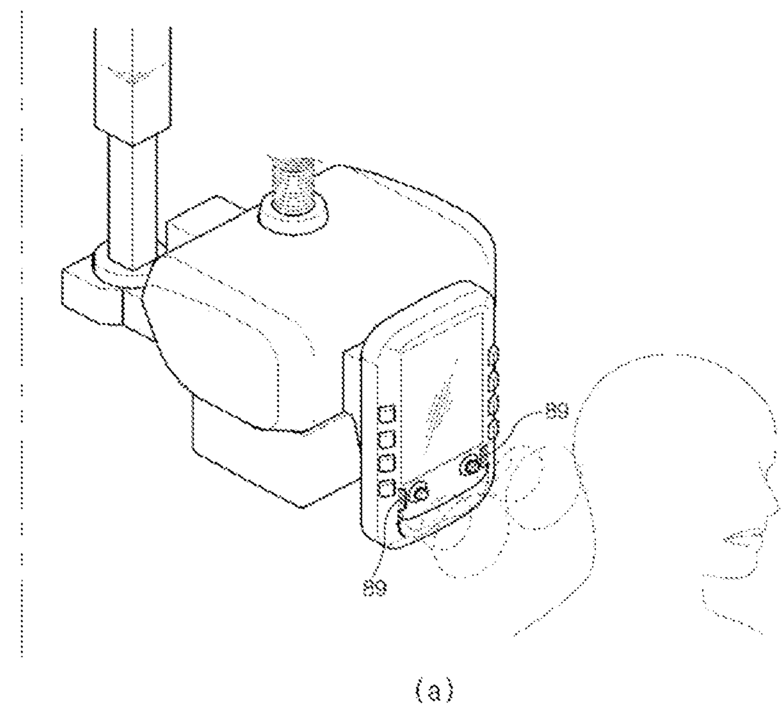
FIG. 6 is a view showing a case in which a sensor installed at an X-ray source detects an object, in accordance with an exemplary embodiment.
Figure 6:
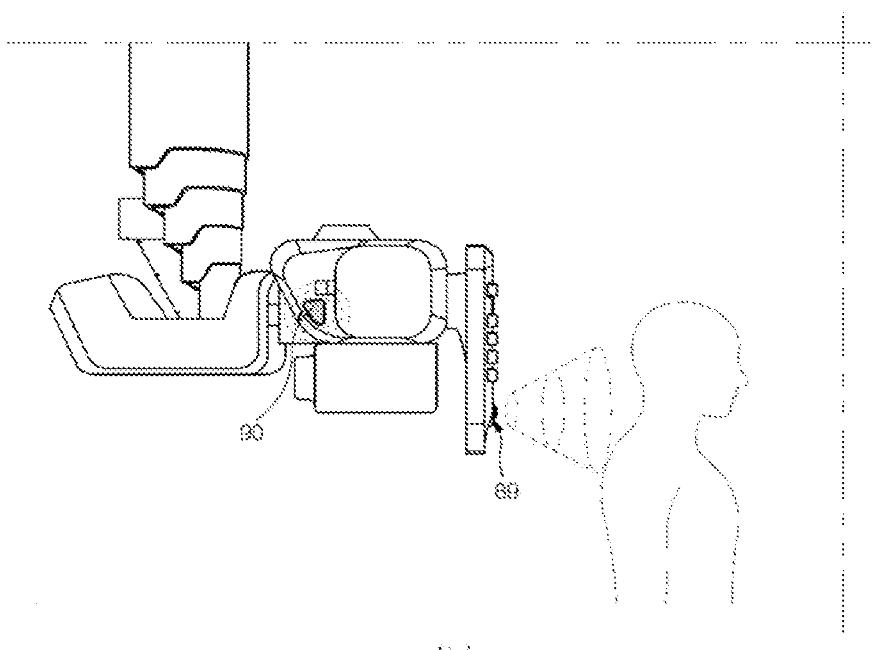

FIG. 6 is a view showing a case in which a sensor installed at an X-ray source detects an object, in accordance with an exemplary embodiment.

As illustrated in drawing (a) of FIG. 6, the sensor 89 may be disposed in the manipulation unit 80 of the X-ray source 70, and as illustrated in drawing (b) of FIG. 6, the sensor 90 may also be disposed on a side of the X-ray source 70 so as to detect the objects placed on the movement path of the X-ray source 70 from the front and sides of the X-ray source 70. Positions of the above-described sensors 89 and 90 are just examples, and positions in which sensors are disposed, or the number of sensors are not limited. In addition, there may be various types of sensors, such as a motion sensor, an image sensor, an infrared sensor, a radio sensor, and a three-dimensional (3D) detection sensor. The sensor may recognize the existence of the object by detecting a predetermined distance between the sensor and the object, as illustrated in FIG. 6. Furthermore, the motion sensor may recognize a motion of a moving object and may acquire a 3D shape of the object, and the image sensor may also acquire a shape of the object. The infrared sensor or radio sensor may measure a distance between the object and the infrared sensor or radio sensor by transmitting infrared rays or radio waves to the object, and when a plurality of sensors are installed, the infrared sensor or radio sensor may detect a one-dimensional distance between the object and the infrared sensor or radio sensor and a two-dimensional (2D) or 3D shape and the position of the object. The 3D detection sensor may recognize a distance between the object and the 3D detection sensor and a 3D shape of the object. When a plurality of sensors that may recognize the one-dimensional distance between the object and the sensor and the shape of the object are installed, the plurality of sensors may detect 2D and 3D shapes and thus may detect 2D and 3D objects according to types and the number of sensors. By using the sensors, as illustrated in FIG. 5, the X-ray source 70 may be moved by detecting and avoiding the objects 1, 2, and 3 on the path on which the X-ray source 70 is moved.

Figure 7:
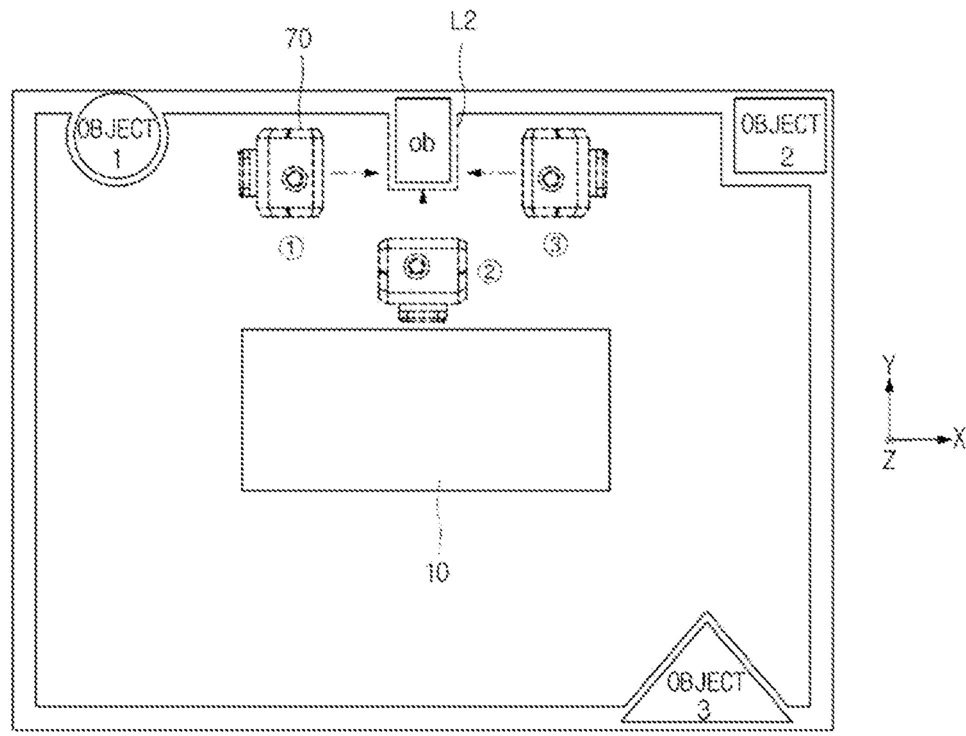
FIG. 7 is a view showing a case in which, when a new object is placed on a path of the X-ray source, the X-ray source is controlled to avoid the object and to be moved, in accordance with an exemplary embodiment.
Figure 7:
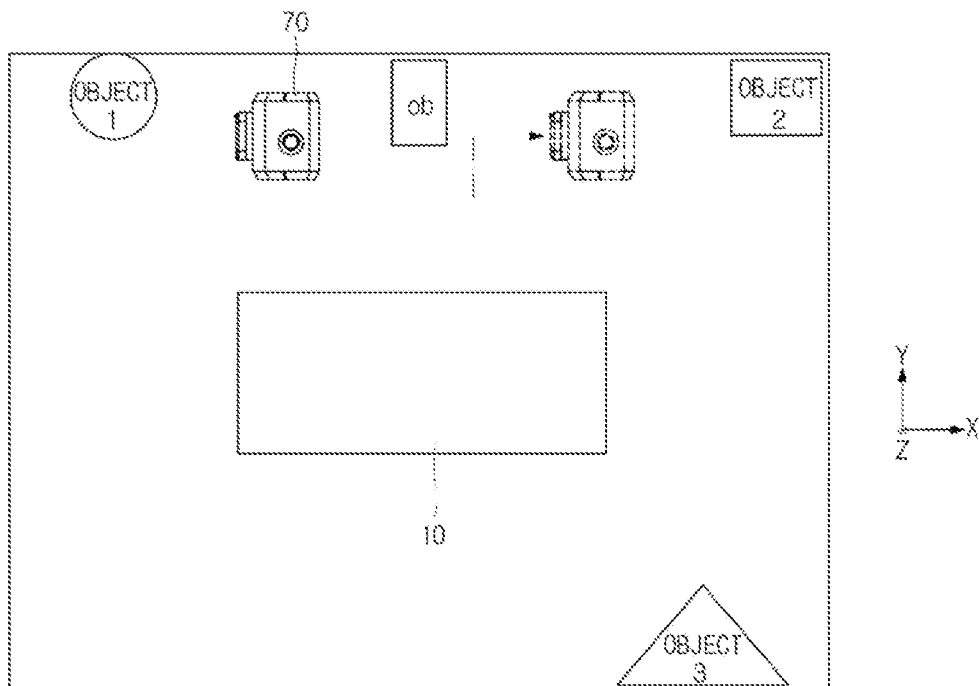

FIG. 7 is a view showing a case in which, when a new object is placed on a path of the X-ray source, the X-ray source is controlled to avoid the object and to be moved, in accordance with an exemplary embodiment.

As illustrated in FIG. 7, a new object ob in addition to the existing objects 1, 2, and 3 may be placed on the moving path of the X-ray source 70. Objects which include the new object ob may be placed somewhere along the movement path of the X-ray source 70. First, the X-ray source 70 is moved such that the X-ray source 70 may be moved so as to avoid the newly-placed object ob. In a movement method, the X-ray source 70 may be moved adjacent to the new object ob by using the above-described automatic movement mode or manual movement mode. When the X-ray source 70 is disposed adjacent to the new object ob, according to the related art, movement of the X-ray source 70 is stopped so as to prevent a collision according to object detection of the sensor 89. However, according to one or more exemplary embodiments, a direction in which the new object ob may be avoided, or an avoidance path thereof, may be set.

When the X-ray source 70 is disposed adjacent to the new object ob, the sensor 89 may recognize the existence of the object and may detect a distance between the new object ob and the sensor 89 and a shape of the new object ob. The user may input control instructions relating to the movement region of the X-ray source 70 by using the manipulation unit 80. The control instructions relating to the movement region may be used to set a movement limitation direction so that the X-ray source 70 may not disposed adjacent to the new object ob, as illustrated in drawing (a) of FIG. 7, or may be used to directly set a path on which the X-ray source 70 may be moved so as to avoid the new object ob, as illustrated in drawing (b) of FIG. 7.

Figure 8:
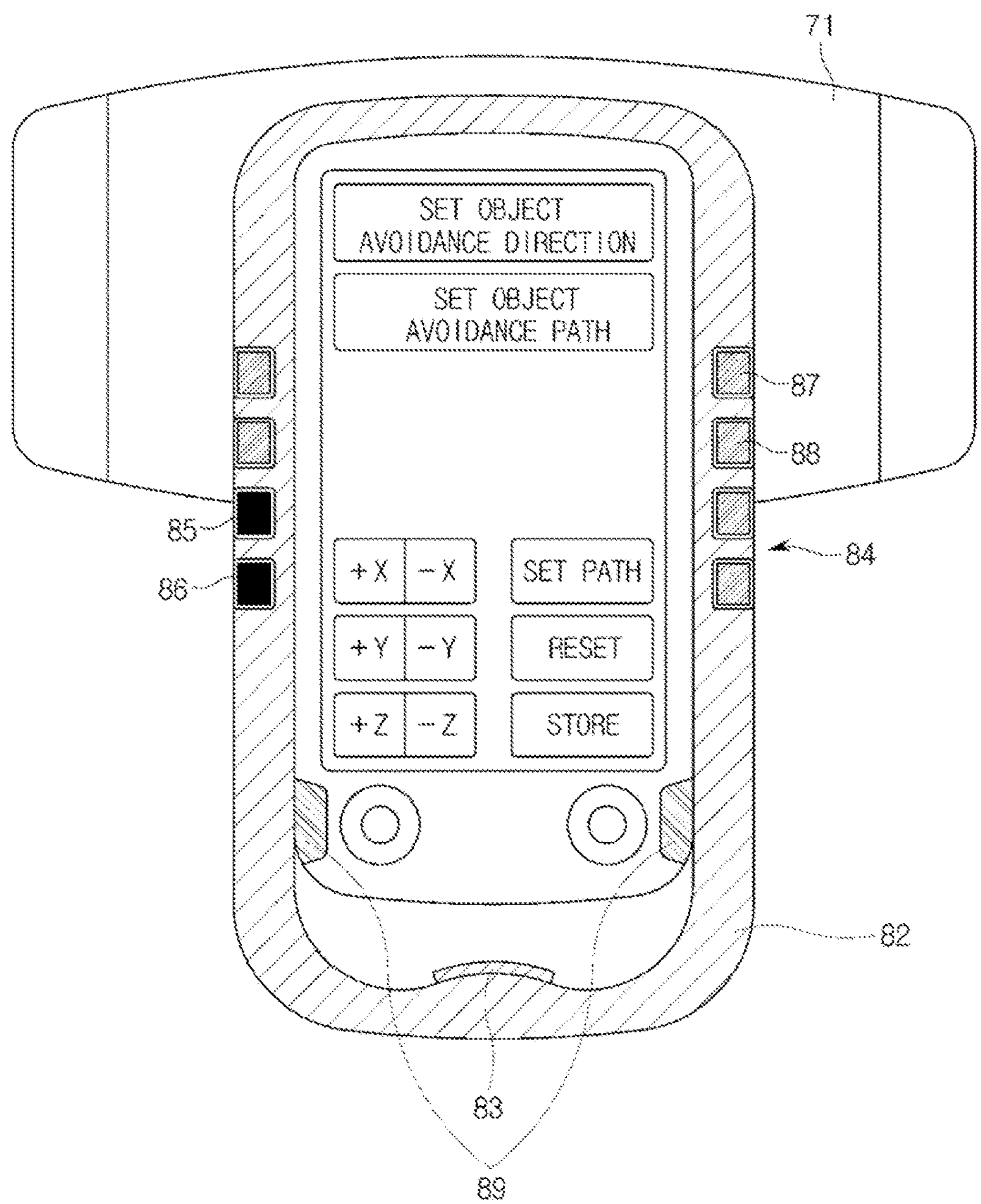
FIG. 8 is a view showing a manipulation unit that provides an interface via which control instructions that relate to enabling the X-ray source to be moved so as to avoid the object are inputtable, in accordance with an exemplary embodiment.

FIG. 8 is a view showing a manipulation unit that provides an interface via which control instructions that relate to enabling the X-ray source to be moved so as to avoid the object are inputtable, in accordance with an exemplary embodiment.

Referring to FIG. 8, a screen via which the user may input the control instructions relating to the movement region of the X-ray source 70 may be displayed on the display unit 81 of the manipulation unit 80. Referring back to FIG. 7, when the X-ray source 70 is moved close to the object ob and is disposed in position ①, if the X-ray source 70 is moved in an +X direction, the X-ray source 70 may collide with the object ob. Thus, the user is required to input the control instructions so that the X-ray source 70 may not be moved in the +X direction. The user may input the control instructions by touching an object avoidance direction setting button on the touch screen of the manipulation unit 80 illustrated in FIG. 8 and by touching an +X direction button so that the X-ray source 70 may not be moved in the +X direction. The control instructions may be input by touching direction setting buttons several times, and several directions may be simultaneously input. The control instructions may be input by using the touch screen displayed on the display unit 81 or by using the physical buttons 84. When a storage button is pressed after direction setting is completed, data that relates to the direction in which movement of the X-ray source 70 input by the user is limited may be stored in the memory 310, and may be used to control a movement of the X-ray source 70.

When the X-ray source 70 is disposed in position CD, if the X-ray source 70 is moved in a +Y direction, the X-ray source 70 may collide with the object ob. Thus, the user may input the control instructions by touching a +Y direction button on the touch screen of the manipulation unit 80 so that the X-ray source 70 may not be moved in the +Y direction. Similarly, when the X-ray source 70 is disposed in position CD, if the X-ray source 70 is moved in a −X direction, the X-ray source 70 may collide with the object ob. Thus, the user may input the control instructions by touching an −X direction button so that the X-ray source 70 may not be moved in the −X direction.

The processor 300 may control the X-ray source 70 not to be moved in a set position in a set direction based on the input control instructions. In this case, it may be determined by the existing movement path of the X-ray source 70 or detection of the sensors 89 and 90 that the X-ray source 70 is currently disposed adjacent to the object ob. In this aspect, the processor 300 may control the motor 110 so that the X-ray source 70 may not be disposed adjacent to a boundary L2 on the periphery of the new object ob. Further, the X-ray source 70 may be controlled to be moved so as to avoid the object ob based on the control instructions stored in the memory 310.

As illustrated in drawing (b) of FIG. 7, the user may also input the control instructions for setting a path on which the X-ray source 70 may be moved so as to avoid the object ob, in addition to setting a direction in which a movement of the X-ray source 70 is limited. The user may move the X-ray source 70 to a path on which the X-ray source 70 avoids the object ob in the manual movement mode or automatic movement mode after pressing an object avoidance path setting button on a control instruction input screen displayed on the display unit 81 of FIG. 8. While the X-ray source 70 is being moved according to object avoidance path setting, the movement path may be stored in the X-ray source 310, and while the X-ray source 70 is later moved based on the stored path, the processor 300 may move the X-ray source 70 so as to avoid the object ob. In drawing (b) of FIG. 7, the path on which the X-ray source 70 is moved so as to avoid the object ob is indicated by an arrow.

When the user directly inputs the control instructions and the sensor 89 detects the object ob while the X-ray source 70 is being moved, the X-ray source 70 may be moved in a direction in which the X-ray source 70 avoids the object ob, based on detection of the sensor 89. In particular, the processor 300 may control the motor 110 by using signals detected by the sensor 89 such that the X-ray source 70 may be moved so as to avoid the object ob. Similarly as in drawing (a) of FIG. 7, when the X-ray source 70 is disposed adjacent to the object ob, signals for limiting movement in a direction in which the X-ray source 70 is disposed adjacent to the object ob may be transmitted to the processor 300, and similarly as in drawing (b) of FIG. 7, a path on which the X-ray source 70 is moved so as to avoid the object ob may also be transmitted to the processor 300 based on a detection of the object ob by the sensor 89. Data that relates to the movement limitation direction of the X-ray source 70 detected by the sensor 89 or the path on which the X-ray source 70 is moved so as to avoid the object ob may be stored in the memory 310.

Figure 9:
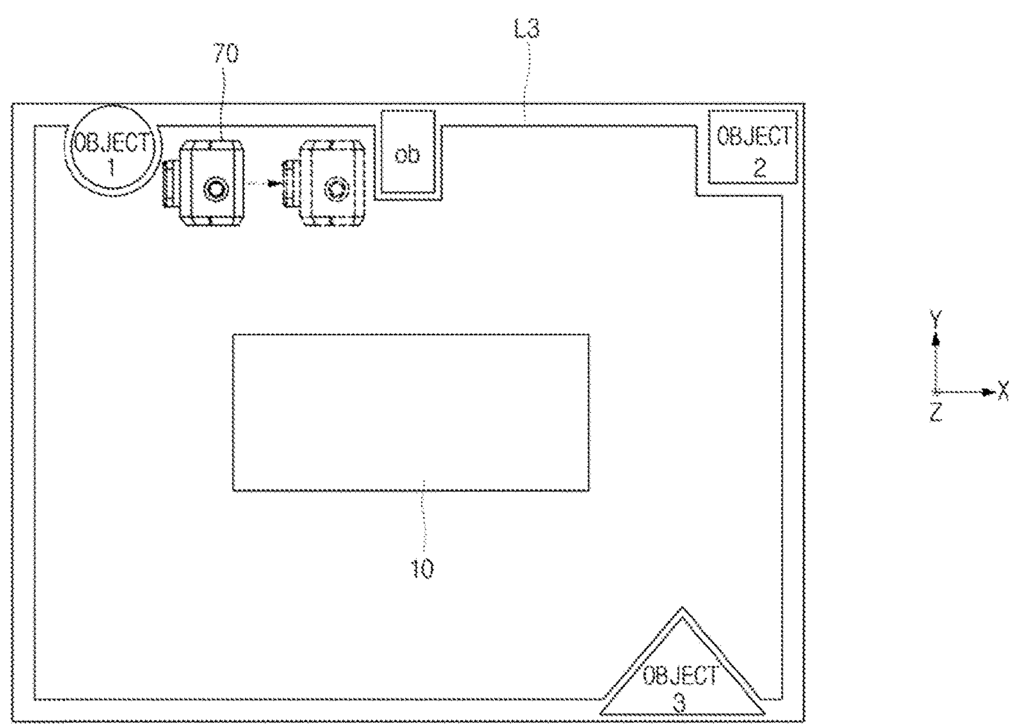
FIG. 9 is a view showing a movement region reset such that the X-ray source is moved so as to avoid a new object, in accordance with an exemplary embodiment.

FIG. 9 is a view showing a movement region reset such that the X-ray source is moved so as to avoid a new object, in accordance with an exemplary embodiment.

As illustrated in FIG. 9, a region which excludes the region in which the new object ob is included may be reset as the movement region of the X-ray source 70 according to the user's control instruction input or detection of the object ob by the sensor 89. A region L3 of FIG. 9 refers to a region in which the X-ray source 70 does not collide with the objects 1,2, and 3 and the new object ob and may be moved. Data that relates to the reset region may be stored in the memory 310, and the processor 300 may limit the movement region L3 of the X-ray source 70 based on the stored data.

Figure 10:
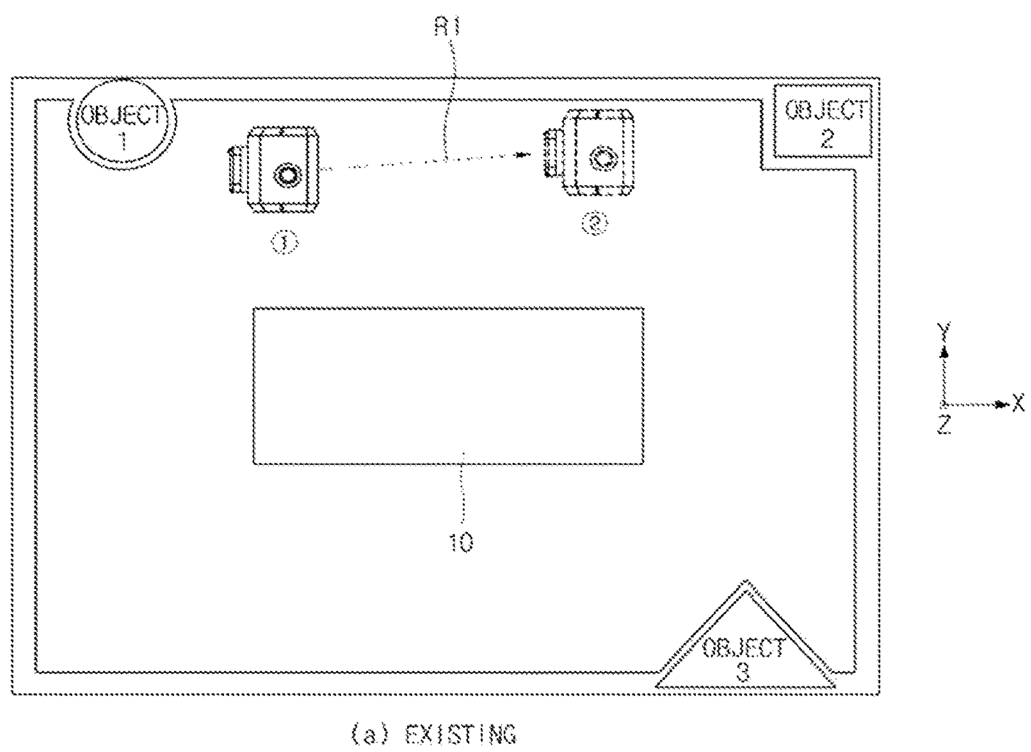
FIG. 10 is a view for describing an operation of setting a shortest path on which the X-ray source is moved to a target point so as to avoid an obstacle, in accordance with an exemplary embodiment.
Figure 10:
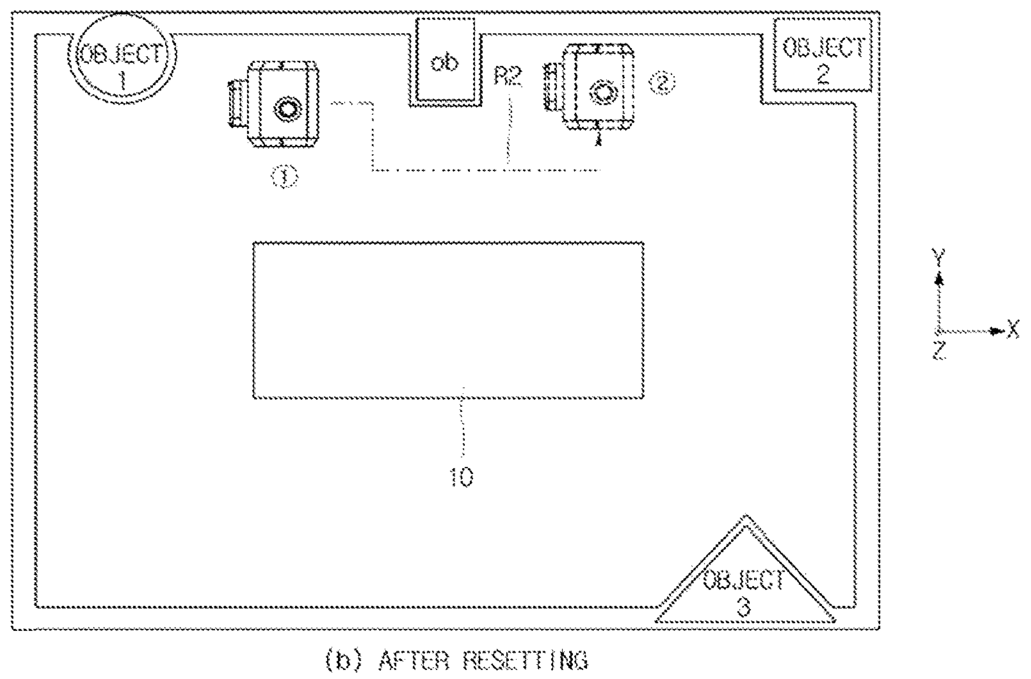

FIG. 10 is a view for describing an operation of setting a shortest path on which the X-ray source is moved to a target point so as to avoid an obstacle, in accordance with an exemplary embodiment.

As illustrated in drawing (a) of FIG. 10, when no new object ob is present according to the related art, a path on which the X-ray source 70 is moved via a path R1 so as to move from position ① to position ② is a shortest path. However, as illustrated in drawing (b) of FIG. 10, when the new object ob exists, the X-ray source 70 has to be moved via a path R2 so as to move from position ① to position ②, in order to avoid the new object ob. The processor 300 may calculate a shortest path R2 on which the X-ray source 70 may reach a target point while avoiding the object ob, based on the control instructions relating to the movement region of the X-ray source 70 input by the user and detection by the sensor 89, and may store the set shortest path in the memory 310. When the X-ray source 70 is disposed adjacent to the object ob, the processor 300 may control the X-ray source 70 to be moved to the shortest path R2 based on the shortest path R2 stored in the memory 310. By resetting the above-described shortest path R2, efficient and fast image capturing and diagnosis may be performed when X-ray imaging is performed.

Figure 11:
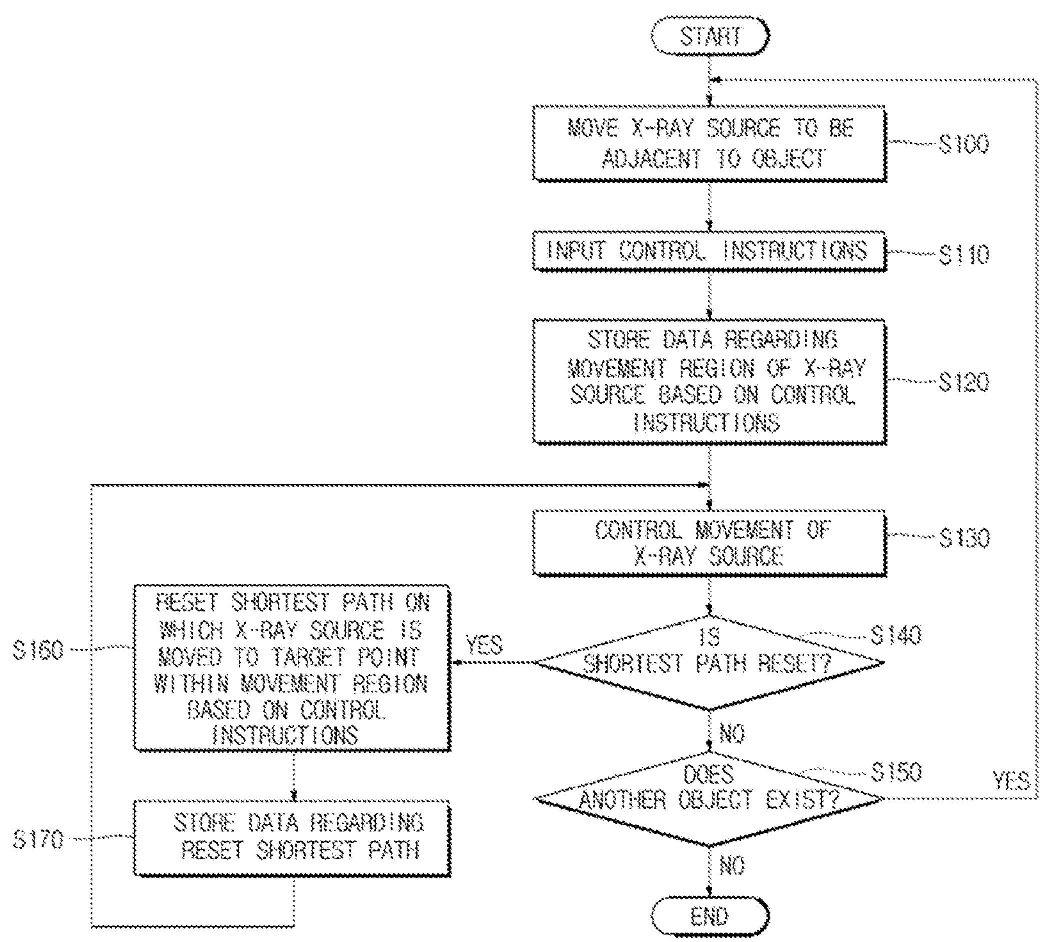
FIG. 11 is a flowchart illustrating a method for controlling an X-ray imaging apparatus, in accordance with an exemplary embodiment.

FIG. 11 is a flowchart illustrating a method for controlling an X-ray imaging apparatus, in accordance with an exemplary embodiment.

As illustrated in FIG. 11, first, in operation S100, the X-ray source 70 may be moved to be adjacent to an object ob. The X-ray source 70 may be moved by the automatic movement mode or manual movement mode, as described above. After the X-ray source 70 is moved to be adjacent to the object ob (obstacle), in operation S110, the user may input control instructions relating to the movement region of the X-ray source 70 by using the manipulation unit 80. The control instructions relating to the movement region of the X-ray source 70 may include control instructions for setting a direction in which movement of the X-ray source 70 is limited, or control instructions for setting a movement path of the X-ray source 70. Data that relates to the movement region of the X-ray source 70 based on the control instructions input by the user may be stored in the memory 310 in operation S120, and the processor 300 may control the X-ray source 70 to be moved in the movement region based on the control instructions input by the user in operation S130. Then, in operation S140, the processor 300 may determine whether to reset the shortest path when the X-ray source 70 is moved so as to avoid the object ob. When the X-ray source 70 is moved to the target point, and if the shortest path has to be changed due to the object ob, then in operation S160, the user may reset the shortest path on which the X-ray source 70 is moved to the target point within the movement region based on the control instructions input by the user. Data regarding the shortest path reset by the processor 300 may be stored in the memory 310 in operation S170. When the shortest path does not need to be reset, in operation S150, the processor 300 may determine whether another obstacle exists on a path on which the X-ray source 70 is moved. When another obstacle exists, the above-described procedure is repeated from operation S100, and when no other obstacle exists, the control operation is terminated. Alternatively, the user may determine whether another obstacle exists, and when another obstacle exists, the above procedure is repeated from operation S100.

Figure 12:
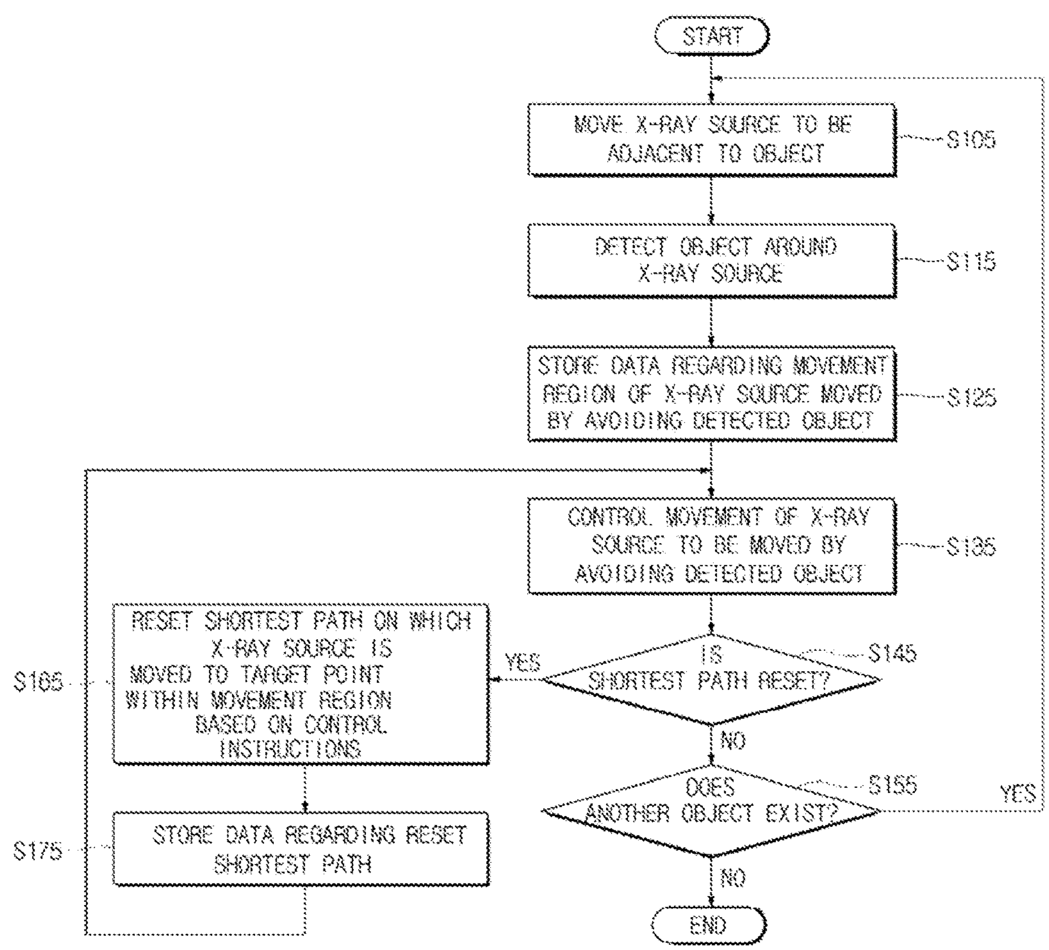
FIG. 12 is a flowchart illustrating a method for controlling an X-ray imaging apparatus, in accordance with another exemplary embodiment.

FIG. 12 is a flowchart illustrating a method for controlling an X-ray imaging apparatus, in accordance with another exemplary embodiment.

As illustrated in FIG. 12, first, in operation S105, the X-ray source 70 may be moved to be adjacent to the object ob. The X-ray source 70 may be moved by the automatic movement mode or the manual movement mode, as described above. While the X-ray source 70 is being moved, in operation S115, the sensor 89 disposed in the periphery of the X-ray source 70 may detect the object ob. The sensor 89 may detect a distance between the X-ray source 70 and the object ob and may continuously detect the object ob while the X-ray source 70 is being moved so as to avoid the object ob. Data that relates to the movement region of the X-ray source 70 moved by avoiding the detected object ob may be stored in the memory 310 in operation S125, and the processor 300 may control the X-ray source 70 to be moved so as to avoid the object ob detected by the sensor 89 in operation S135. Then, in operation S145, the processor 300 may determine whether the shortest path is reset when the X-ray source 70 is moved so as to avoid the object ob. When the X-ray source 70 is moved to the target point, if the shortest path has to be changed due to the object ob, in operation S165, the X-ray source 70 may reset the shortest path on which the X-ray source 70 is moved to the target point so as to avoid the detected object ob. The data that relates to the shortest path reset by the processor 300 may be stored in the memory 310 in operation S175. When the shortest path does not need to be reset, in operation S155, the processor 300 may determine whether another object detected by the sensor 89 exists on the path on which the X-ray source 70 is moved. When another object exists, the above procedure is repeated from operation S105, and when no other object exists, the control operation is terminated.

Figure 13:
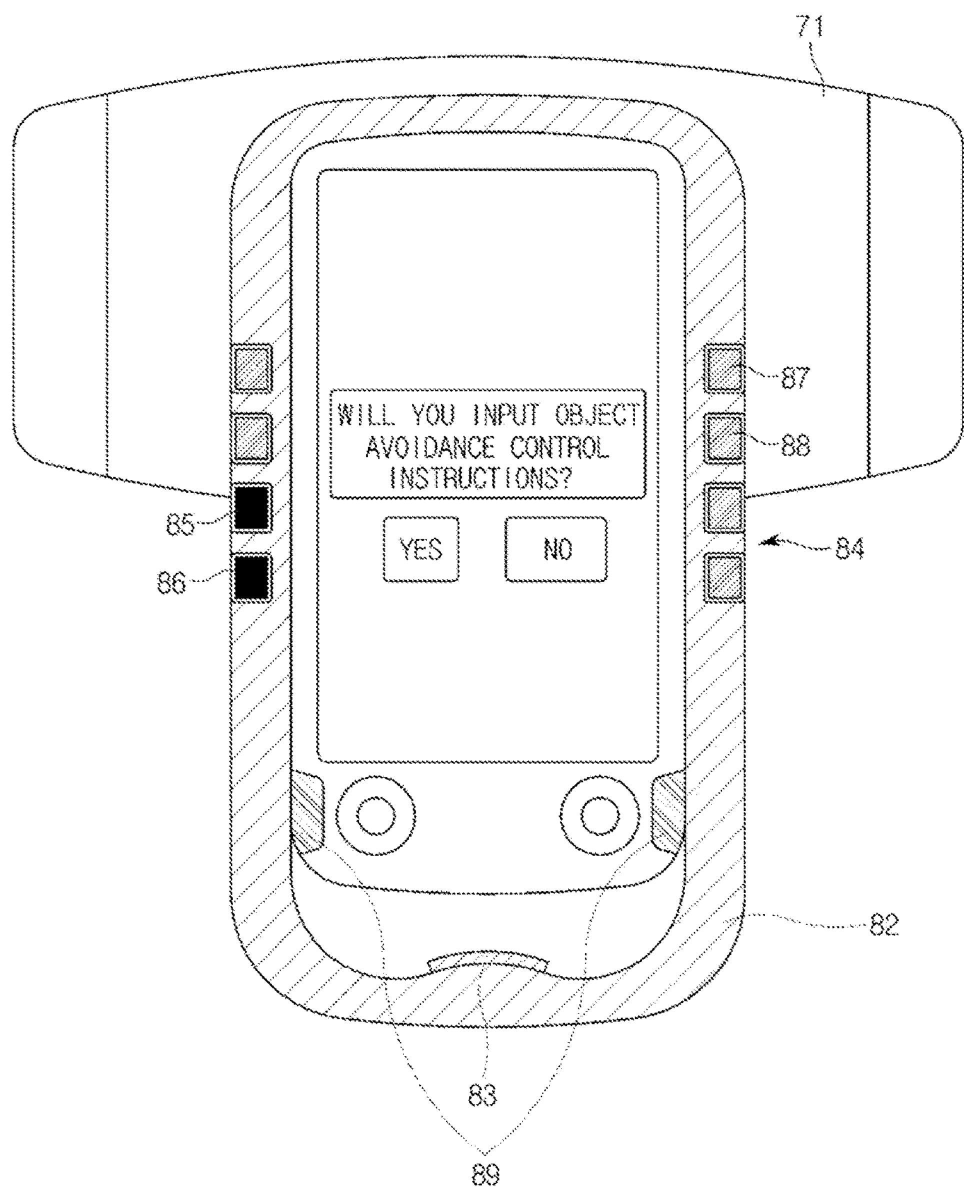
FIG. 13 is a view of a screen on which an interface via which control instructions are capable of being input so that the X-ray source avoids an object as a sensor detects the object, is displayed, in accordance with an exemplary embodiment.

FIG. 13 is a view of a screen on which an interface via which control instructions are capable of being input so that the X-ray source avoids an object as a sensor detects the object is displayed, in accordance with an exemplary embodiment.

As described above in FIGS. 11 and 12, when the X-ray source 70 is disposed adjacent to the object ob, the user may input control instructions so that the X-ray source 70 may be moved so as to avoid the object ob, and the sensor 89 may transmit control signals to the processor 300 such that the X-ray source 70 may be moved so as to avoid the object ob without the user's input of the control instructions as the sensor 89 detects the object ob.

As illustrated in FIG. 13, a screen via which the user may input the control instructions may be displayed on the display unit 81 of the manipulation unit 80 such that the X-ray source 70 may be moved so as to avoid the object ob. In particular, after the X-ray source 70 is moved to be adjacent to the object ob, signals detected when the sensor 89 detects the object ob may not be controlled to be transmitted to the processor 300, but an input interface may be provided to the display unit 81 so that the user may input the control instructions based on object detection by the sensor 89. When the X-ray source 70 may not be moved in a direction in which the sensor 89 detects the object ob or the X-ray source 70 should be moved so as to avoid the object ob, as shown in the screen of FIG. 13, if the screen via which the user may input object avoidance control instructions is displayed and the user inputs the control instructions accordingly, the method for controlling the X-ray imaging apparatus from operation S110 of FIG. 11 may be implemented. That is, FIG. 13 illustrates the method for controlling the X-ray imaging apparatus, whereby the sensor 89 detects the obstacle, the user directly inputs the object avoidance control instructions and the X-ray source 70 may be controlled to be moved so as to avoid the object, in accordance with an exemplary embodiment.

As described above, in an X-ray imaging apparatus and a method for controlling the same according to the one or more of the above-described exemplary embodiments, a path on which an X-ray source avoids an obstacle is automatically set on a movement path of the X-ray source, or a user manually sets the path on which the X-ray source avoids the obstacle by using a simple manipulation so that safe and fast X-ray imaging can be performed.

As disclosed above, the X-ray imaging apparatus and the method for controlling the same according to the exemplary embodiments have been described with reference to the drawings. In the above-described exemplary embodiments of the X-ray imaging apparatus and the method for controlling the same, when a new object exists on a movement path of an X-ray source and becomes an obstacle, a sensor disposed in the X-ray source detects the object, and an object avoidance path may be automatically set, or a user may input control instructions relating to an avoidance path so that the X-ray source can be controlled to be moved so as to avoid the obstacle. In this aspect, even when an engineer does not additionally reset the movement path of the X-ray source so as to avoid the new object, the user may simply set the object avoidance path so that X-ray imaging and diagnosis can be efficiently performed. Examples of the X-ray imaging apparatus and the method for controlling the same are not limited thereto, and the above-described exemplary embodiments are illustrative in all aspects.

Although a few exemplary embodiments have been shown and described, it will be appreciated by those of ordinary skill in the art that changes may be made in these exemplary embodiments without departing from the principles and spirit of the present inventive concept, the scope of which is defined in the claims and their equivalents.

What is claimed is:

1. An X-ray imaging apparatus comprising:

an X-ray source which is movably disposed;

an input device configured to receive at least one from among a first control instruction and a second control instruction relating to setting of a movement region of the X-ray source in an operation room; and a processor configured to control a movement of the X-ray source and to set the movement region of the X-ray source based on the at least one control instruction, wherein the first control instruction includes a movement direction such that when an object exists adjacent to the X-ray source and in response to the first control instruction being received, the processor is further configured to limit the movement of the X-ray source in the movement direction, and wherein the second control instruction includes an instruction to set an avoidance path such that when the object exists in a movement path of the X-ray source and in response to the second control instruction being received, the processor is further configured to set the avoidance path and to control the movement of the X-ray source to avoid the object based on the set avoidance path.

2. The X-ray imaging apparatus of claim 1, wherein the input device comprises a touch screen that is disposed within a predetermined proximity of the X-ray source and that is configured to provide an interface via which the at least one control instruction is inputtable.

3. The X-ray imaging apparatus of claim 1, wherein the input device is further configured to receive at least one additional instruction that relates to resetting the movement region of the X-ray source as a region that excludes the object that exists in the movement path of the X-ray source.

4. The X-ray imaging apparatus of claim 3, wherein the input device comprises:

a first button via which at least one instruction relating to a control mode of the movement region is inputtable; and a second button via which at least one instruction relating to storing data that relates to the movement region of the X-ray source based on the at least one control instruction is inputtable.

5. The X-ray imaging apparatus of claim 4, wherein, if the first button is manipulated, the at least one from among the first control instruction that relates to setting a direction in which a movement of the X-ray source is limited and the second control instruction that relates to setting a movement path of the X-ray source is received, and each of the first button and the second button comprises at least one from among a physical input unit, a touch screen, and a remote controller.

6. The X-ray imaging apparatus of claim 3, wherein the processor is further configured to reset a shortest path on which the X-ray source is moved to a target point within the movement region based on the at least one additional control instruction, and to control the movement of the X-ray source so that the X-ray source is moved based on the reset shortest path.

7. The X-ray imaging apparatus of claim 6, further comprising a memory configured to store data that relates to the movement region of the X-ray source based on the at least one additional control instruction.

8. The X-ray imaging apparatus of claim 7, wherein the memory is further configured to store data that relates to the reset shortest path.

9. An X-ray imaging apparatus comprising:

an X-ray source which is movably disposed;

a sensor configured to detect an object which is disposed within a first predetermined proximity of the X-ray source;

an input device configured to, in response to the sensor detecting the object which is disposed within the first predetermined proximity of the X-ray source, receive an instruction from a user, the instruction including one from among an instruction to manually avoid the object and an instruction to automatically avoid the object; and a processor configured to, in response to the instruction from the user including the instruction to automatically avoid the object, calculate a shortest path on which the X-ray source is movable to a target point while avoiding the object, and to control a movement of the X-ray source such that when the object is detected by the sensor, the X-ray source is moved based on the shortest path calculated by the processor, and to set a movement region of the X-ray source based on at least one control instruction relating to setting of the movement region of the X-ray source in an operation room.

10. The X-ray imaging apparatus of claim 9, wherein the input device is further configured to, in response to the instruction from the user including the instruction to manually avoid the object, receive at least one from among a first control instruction that relates to setting a direction in which the movement of the X-ray source is limited, and a second control instruction that relates to setting a movement path of the X-ray source.

11. The X-ray imaging apparatus of claim 9, wherein the sensor is disposed within a second predetermined proximity of the X-ray source and comprises at least one from among a motion sensor, an image sensor, an infrared sensor, a radio sensor, and a three-dimensional (3D) detection sensor.

12. The X-ray imaging apparatus of claim 9, wherein the sensor is further configured to detect a distance between the X-ray source and the object and to detect the object while the X-ray source is being moved so as to avoid the object.

13. The X-ray imaging apparatus of claim 9, wherein the processor is further configured to reset a shortest path on which the X-ray source is moved to a target point while avoiding the object, and to control a movement region of the X-ray source such that the X-ray source is moved based on the reset shortest path.

14. The X-ray imaging apparatus of claim 13, further comprising a memory configured to store data that relates to the movement region of the X-ray source.

15. The X-ray imaging apparatus of claim 14, wherein the memory is further configured store data that relates to the reset shortest path.

16. A method for controlling an X-ray imaging apparatus, the method comprising:

moving an X-ray source to be adjacent to an object;

receiving at least one from among a first control instruction and a second control instruction relating to setting of a movement region of the X-ray source in an operation room; and controlling a movement of the X-ray source and setting the movement region of the X-ray source based on the received at least one control instruction, wherein the first control instruction includes a movement direction such that when the object is adjacent to the X-ray source and in response to the first control instruction being received, the controlling the movement of the X-ray source comprises limiting the movement of the X-ray source in the movement direction, and wherein the second control instruction includes an instruction to set an avoidance path such that when the object exists in a movement path of the X-ray source and in response to the second control instruction being received, the controlling the movement of the X-ray source comprises setting the avoidance path and controlling the movement of the X-ray source to avoid the object based on the set avoidance path.

17. The method of claim 16, wherein the method further comprises receiving at least one additional control instruction that relates to resetting the movement region of the X-ray source as a region that excludes the object that exists in the movement path of the X-ray source, and wherein the controlling the movement of the X-ray source comprises resetting a shortest path on which the X-ray source is moved to a target point within the movement region based on the received at least one additional control instruction and controlling the movement of the X-ray source such that the X-ray source is moved based on the reset shortest path.

18. The method of claim 17, further comprising storing data that relates to the movement region of the X-ray source based on the received at least one additional control instruction.

19. The method of claim 18, wherein the storing the data further comprises storing data that relates to the reset shortest path.

20. A method for controlling an X-ray imaging apparatus, the method comprising:

moving an X-ray source to be adjacent to an object;

detecting the object that is disposed within a predetermined proximity of the X-ray source;

receiving, in response to detecting the object that is disposed within the predetermined proximity of the X-ray source, an instruction from a user, the instruction including one from among an instruction to manually avoid the object and an instruction to automatically avoid the object;

calculating, in response to the instruction from the user including the instruction to automatically avoid the object, a shortest path on which the X-ray source is movable to a target point while avoiding the second object; and controlling a movement of the X-ray source such that the X-ray source is moved based on the calculated shortest path, and setting a movement region of the X-ray source based on at least one control instruction relating to setting of the movement region of the X-ray source in an operation room.

21. The method of claim 20, wherein the detecting the object comprises detecting a distance between the X-ray source and the object and detecting the object while the X-ray source is being moved so as to avoid the object.

22. The method of claim 20, wherein the controlling the movement of the X-ray source comprises resetting the shortest path on which the X-ray source is moved to the target point so as to avoid the detected object and controlling the movement of the X-ray source such that the X-ray source is moved based on the reset shortest path.

23. The method of claim 22, further comprising storing data that relates to a movement region of the X-ray source.

24. The method of claim 23, wherein the storing the data comprises storing data that relates to the reset shortest path.

* * * * *